(12) United States Patent
Snyder et al.

(10) Patent No.: US 8,017,829 B1
(45) Date of Patent: Sep. 13, 2011

(54) SELECTIVE EXPRESSION OF GENES IN PLANTS

(75) Inventors: John R. Snyder, West Lafayette, IN (US); Thomas K. Hodges, West Lafayette, IN (US); Leszek A. Lyznik, Johnston, IA (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 09/486,904

(22) PCT Filed: Sep. 3, 1998

(86) PCT No.: PCT/US98/18416
§ 371 (c)(1),
(2), (4) Date: Mar. 3, 2000

(87) PCT Pub. No.: WO99/11807
PCT Pub. Date: Mar. 11, 1999

Related U.S. Application Data (60) Provisional application No. 60/057,982, filed on Sep. 5, 1997.

(51) Int. Cl.
*C12N 15/82* (2006.01)
*A01H 5/00* (2006.01)

(52) U.S. Cl. .................. 800/278; 800/260; 800/288

(58) Field of Classification Search ............ 435/6, 69.1, 435/70.1, 183, 419, 320.1; 530/370, 350; 536/23.1, 23.2, 23.7, 24.1, 24.2; 800/278, 800/288, 295
See application file for complete search history.

(56) References Cited

U.S. PATENT DOCUMENTS

| 5,658,772 | A | 8/1997 | Odell et al. |
| 6,392,119 | B1 * | 5/2002 | Gutterson et al. |

FOREIGN PATENT DOCUMENTS

| WO | 96/04393 | 2/1996 |
| WO | 97/13401 | 4/1997 |

OTHER PUBLICATIONS

Birch, RG. Plant Transformation: Problems and Strategies for Practical Application. (1997) Annu. Rev. Plant Physiol. Plant Mol. Biol. 48: 297-326.*
Kilby, NJ et al, Site specific recombinases: tools for genome engineering. (1993) Trends in Genetics, 9: 413-421.*
Gidoni, D. et al, Supplement to Plant Molecular Biology Reporter 18:2, S 03-40; ISPMB abstracts, Jun. 18-24, 2000.*
(Gidoni, D et al (2001) Euphytica 121: 145-156.*
Vergunst (Nucleotide. Acids. Research, 1998, vol. 26, pp. 2729-2734.*
Kilby et al. "FLP Recombinase in Transgenic Plants: Constitutive Activity in Stably Transformed Tobacco and Generation of Marked Cell Clones in Arabidopsis," *Plant Journal*, vol. 8, No. 5, 1995, pp. 637-652.
Lloyd et al. "Functional Expression of the Yeast FLP/FRT Site-specific Recombination System in Nicotiana Tabaccum," *Molecular and General Genetics*, vol. 242, 1994, pp. 653-657.
Lyznik et al. "Activity of Yeast FLP Recombinase in Maize and Rice Protoplasts" *Nucleic Acids Research*, Feb. 25, 1993, pp. 969-975.
Lyznik et al. "Heat-inducible Expression of FLP Gene in Maize Cells," *Plant Journal*, Aug. 1995, 8(2), pp. 177-186.
Kamo et al. "Embryogenic Callus Formation from Maize Protoplasts," *Planta*, vol. 172, 1987, pp. 245-251.
Bradford, "A Rapid Sensitive Method for the Quantitation of Microgram Quantities of Protein Utilizing the Principle of Protein-dye Binding," *Analytical Biochemistry*, vol. 72, 1976, pp. 248-254.
Shockett, P. and Schatz, D. "Switching on Gene Expression," *Nature Biotechnology*, vol. 15, Mar. 1997, pp. 219-221.

* cited by examiner

*Primary Examiner* — Cathy Kingdon Worley
(74) *Attorney, Agent, or Firm* — Barnes & Thornburg LLP (57) ABSTRACT

This invention relates to a method of biocatalytically producing compounds that are commercially valuable but are detrimental to the host cells' development. The transgenic plants produced in accordance with the present invention comprise a novel controlled expression system comprising a promoter (2), a blocking sequence (a), and a structural gene (6), wherein the blocking sequence (a) is flanked by a pair of directly repeated site-specific recombination sequences (4). The blocking sequence (a) prevents expression of the structural gene (6) until removal of the blocking sequence (a) by site-specific recombinase activity encoded by a site-specific recombinase gene (12).

7 Claims, 5 Drawing Sheets

SEQUENCE LISTING

<160> NUMBER OF SEQ ID NOS: 9

<210> SEQ ID NO 1
<211> LENGTH: 42
<212> TYPE: DNA
<213> ORGANISM: Saccharomyces cerevisiae -continued

```
<400> SEQUENCE: 1
gtgatcagaa gttcctattc cgaagttcct attctctaga aa                    42

<210> SEQ ID NO 2
<211> LENGTH: 28
<212> TYPE: DNA
<213> ORGANISM: Saccharomyces cerevisiae

<400> SEQUENCE: 2
ctgatcagaa gttcctatac tttctaga                                   28

<210> SEQ ID NO 3
<211> LENGTH: 13
<212> TYPE: DNA
<213> ORGANISM: Zea mays

<400> SEQUENCE: 3
ccccaacctc gtc                                                   13

<210> SEQ ID NO 4
<211> LENGTH: 17
<212> TYPE: DNA
<213> ORGANISM: Escherichia coli

<400> SEQUENCE: 4
ggggtttcta caggacg                                               17

<210> SEQ ID NO 5
<211> LENGTH: 20
<212> TYPE: DNA
<213> ORGANISM: Zea mays

<400> SEQUENCE: 5
cccgtgcagc tgcggtggca                                            20

<210> SEQ ID NO 6
<211> LENGTH: 26
<212> TYPE: DNA
<213> ORGANISM: Zea mays

<400> SEQUENCE: 6
caactgcagc ccaagcttcc accatg                                     26

<210> SEQ ID NO 7
<211> LENGTH: 56
<212> TYPE: DNA
<213> ORGANISM: Zea mays

<400> SEQUENCE: 7
cttctgcagg tcgactctag gatccccggg ttcgaaatcg ataagcttcc accatg    56

<210> SEQ ID NO 8
<211> LENGTH: 54
<212> TYPE: DNA
<213> ORGANISM: Saccharomyces cerevisiae

<400> SEQUENCE: 8
gatcagaagt tcctatactt tctagagaat aggaacttcg gaataggaac ttct      54
```

```
<210> SEQ ID NO 9
<211> LENGTH: 41
<212> TYPE: DNA
<213> ORGANISM: Saccharomyces cerevisiae

<400> SEQUENCE: 9
gatcagttcc tatactttct agagaatagg aacttcggaa t                           41
```

SELECTIVE EXPRESSION OF GENES IN PLANTS

CROSS-REFERENCES TO RELATED APPLICATIONS

This application is a U.S. national application of international application serial No. PCT/US98/18416 filed Sep. 3, 1998, which claims priority to U.S. provisional application Ser. No. 60/057,982 filed Sep. 5, 1997.

GOVERNMENT RIGHTS

This invention was made with United States Government support under United States Department of Agriculture Grant No. 91-37301-6375. The U.S. Government has certain rights in the invention.

FIELD OF THE INVENTION

This invention relates to a method of biocatalytically producing commercially desirable materials in plants. More particularly the method comprises genetically engineering a plant to contain a gene that is silent during seed multiplication and activated during the last generation of seed production.

BACKGROUND AND SUMMARY OF THE INVENTION

Recombinant DNA technology has been utilized to generate transgenic plants that express desirable phenotypic traits and protein products. However, the production of specialty chemicals such as fatty acids, amino acids, specialty plastic-like compounds, unique peptide hormones, etc. in seeds of plants often causes loss of seed viability and germination. This represents a major impediment to the development of biosynthetic strategies for producing commercially important products in plants because seed multiplication is essential for large-scale commercial production. The present invention is directed to the production of genetically engineered plants having a desired gene that is silent during seed multiplication but is capable of being activated to express its encoded gene product once sufficient numbers of transgenic plants have been generated.

The expression of a gene is generally directed by its own promoter, although other DNA regulatory elements are necessary for efficient expression of a gene product. Promoter sequence elements include the TATA box consensus sequence (TATAAT), which is usually 20 to 30 base pairs (bp) upstream of the transcription start site. In most instances the TATA box is required for accurate transcription initiation.

Promoters can be either constitutive or inducible. A constitutive promoter controls transcription of a gene at a constant rate during the life of a cell, whereas an inducible promoter's activity fluctuates as determined by the presence (or absence) of a specific inducer. The regulatory elements of an inducible promoter are usually located further upstream of the transcriptional start site than the TATA box. Ideally, for experimental purposes, an inducible promoter should possess each of the following properties: a low to nonexistent basal level of expression in the absence of inducer, a high level of expression in the presence of inducer, and an induction scheme that does not otherwise alter the physiology of the cell. The basal transcriptional activity of all promoters can be increased by the presence of "enhancer" sequences. Although the mechanism is unclear, certain defined enhancer regulatory sequences are known, to those familiar with the art, to increase a promoter's transcription rate when the sequence is brought in proximity to the promoter.

The creation of a transformed cell requires that the DNA be physically placed within the host cell. Current transformation procedures utilize a variety of techniques to introduce DNA into a cell. In one form of transformation, the DNA is microinjected directly into cells though the use of micropipettes. Alternatively, high velocity ballistics can be used to propel small DNA associated particles into the cell. In another form, the cell is permeablized by the presence of polyethylene glycol, thus allowing DNA to enter the cell through diffusion. DNA can also be introduced into a cell by fusing protoplasts with other entities which contain DNA. These entities include minicells, cells, lysosomes or other fusible lipid-surfaced bodies. Electroporation is also an accepted method for introducing DNA into a cell. In this technique, cells are subject to electrical impulses of high field strength which reversibly permeabilize biomembranes, allowing the entry of exogenous DNA sequences.

In addition to these "direct" transformation techniques, transformation can be performed via bacterial infection using *Agrobacterium tumafaciens* or *Agrobacterium rhizogenes*. These bacterial strains contain a plasmid (called Ti or Ri respectively) which is transmitted into plant cells after infection by *Agrobacterium*. One portion of the plasmid, named transferred DNA (T-DNA), is then integrated into the genomic DNA of the plant cell. This system has been extensively described in the literature and can be modified to introduce foreign genes and other DNA sequences into plant cells.

Transformed cells (those containing the DNA inserted into the host cell's DNA) can be selected from untransformed cells if a selectable marker (or visible marker) was included as part of the introduced DNA sequences. Selectable markers include genes that provide antibiotic resistance or herbicide resistance. Cells containing these genes are capable of surviving in the presence of antibiotic or herbicide concentrations that kill untransformed cells. Examples of selectable markers include the bar gene which provides resistance to the herbicide Basta, the nptII gene which confers kanamycin resistance and the hpt gene which confers hygromycin resistance. Visible marker genes express products that enable a visual identification of host cells, and thus allow for the identification of cells transformed with the visible marker gene.

Once a transformed plant cell is generated, an entire plant can be obtained through cell culturing techniques. Individual cultured cells divide to give rise to an undifferentiated mass of cells called callus tissue. Once callus tissue is formed, shoots and roots may be induced from the callus by techniques known to those familiar with the art, and the resulting plantlets can be planted. Alternatively, somatic embryo formation can be induced in the callus tissue. These somatic embryos germinate as natural embryos to form plants.

In accordance with the present invention the expression of commercially valuable products that have a detrimental impact on plant cell development is controlled to minimize the negative impact on the plant while maximizing the production of the product. The controlled expression of a desired gene product can be achieved by operably linking the coding sequence of the gene to an inducible promoter. In particular, inducible promoters can be utilized to achieve selective and timed gene expression in plants. For example, a chemically-induced gene promoter can be linked to a desired gene, and plant cells can be transformed with the promoter/gene construct to produce a transgenic plant. The transgenic plant can then be sprayed with the appropriate chemical to induce expression of the gene during the desired stage of development.

A strategy based on the use of environmentally controlled inducible promoters suffers from several disadvantages: 1) the limited number of possible promoters (e.g., heat shock promoter, copper inducible promoter), and 2) the problems associated with treating large numbers of plants in a natural environment. In addition, many inducible genes tend to be "leaky", that is the promoters will express low levels of the gene product even in the absence of the inducer. The present invention eliminates the need for an external treatment to induce selective gene expression and provides and inexpensive approach to producing commercially valuable products in plants wherein the products have a detrimental impact on plant development.

The present invention utilizes site-specific recombinase systems (FLP/FRT, Cre/Lox, etc.) to control the expression of recombinant gene products in plants. In particular, a transgenic plant is generated that contains the desired gene, but the expression of the gene is blocked by a "blocking sequence". In accordance with one embodiment the blocking sequence comprises one or more stop codons that prevent expression of the gene. The site-specific recombinase system is utilized to excise the blocking sequence and thus allow the expression of the gene in a controlled manner.

A number of different site-specific recombinase systems can be used, including but not limited to the Cre/lox system of bacteriophage P1, the FLP/FRT system of yeast, the Gin recombinase of phage Mu, the Pin recombinase of E. coli, and the R/RS system of the pSR1 plasmid. The two preferred site-specific recombinase systems are the bacteriophage P1 Cre/lox and the yeast FLP/FRT systems. In these systems a recombinase (Cre or FLP) will interact specifically with its respective site-specific recombination sequence (lox or FRT respectively) to invert or excise the intervening sequences. The sequence for each of these two systems is relatively short (34 bp for lox and 47 bp for FRT). Currently the FLP/FRT system of yeast is the preferred site-specific recombinase system since it normally functions in a eukaryotic organism (yeast), and is well characterized. Applicants have reason to believe that the eukaryotic origin of the FLP/FRT system allows the FLP/FRT system to function more efficiently in eukaryotic cells than the prokaryotic site-specific recombinase systems.

Depending on the orientation of the site-specific recombination sequences, intervening sequences will either be excised or inverted in the presence of the site-specific recombinase. When the site-specific recombination sequences are orientated in opposite directions relative to one another (i.e., inverted repeats) then any intervening sequences will be inverted relative to the other sequences in the genome. However, if the site-specific recombination sequences are orientated in the same direction relative to one another (i.e., direct repeats) any intervening sequences will be deleted upon interaction with the site-specific recombinase.

The FLP/FRT recombinase system has been demonstrated to function efficiently in plant cells. Experiments on the performance of the FLP/FRT system in both maize and rice protoplasts indicates that FRT site structure, and amount of the FLP protein present, affects excision activity. In general, short incomplete FRT sites leads to higher accumulation of excision products than the complete full-length FRT sites. Site-specific recombination systems can catalyze both intra- and intermolecular reactions in maize protoplasts, indicating that the system can be used for DNA excision as well as integration reactions. The recombination reaction is reversible and this reversibility can compromise the efficiency of the reaction in each direction. Altering the structure of the site-specific recombination sequences is one approach to remedying this situation. The site-specific recombination sequence can be mutated in a manner that the product of the recombination reaction is no longer recognized as a substrate for the reverse reaction, thereby stabilizing the excision event.

Another approach to manipulate the system is based on the entropic advantage of a unimolecular (excision) over a bimolecular (integration) reaction. By limiting the expression of the recombinase enzyme, the efficiency of the integrative recombination, the thermodynamically least favored event, can be reduced. Experiments in maize protoplasts indicate higher concentration of the FLP protein increased the efficiency of the excision reaction.

The use of a site-specific recombinase system to control the expression of gene products allows for the commercial production of useful plant products in economical quantities with environmentally acceptable procedures. The invention is based in part on the ability of a recombinase system to excise a sequence of DNA that separates a promoter from the gene of interest. The excision event operably links the promoter to the gene, thus enabling the expression of the gene. The gene can thus be maintained in a silent state (unexpressed) for any number of generations and then activated by excision of the blocking fragment of DNA, at any desired time and in any number of plants, by crossing the plants containing the "blocked" gene of interest with a plant expressing the site-specific recombinase (FLP, Cre, etc.).

In accordance with one embodiment the disclosed method allows a plant to express one or more genes encoding natural products in concentrations that are deleterious to normal plant or seed development (e.g., a fatty acid or an animal peptide hormone). Alternatively, the present method also allows a plant to express one or more genes encoding foreign products that are deleterious at even low concentrations to normal plant or seed development (e.g., a plastic molecule). Finally, the present invention also allows a plant to express one or more genes which alter normal plant metabolism or development in such a way that the changes are harmful to normal plant or seed development (e.g., inhibit embryo formation, seed germination), and allows a hybrid plant to reproduce by a means that is different from its parent lines (e.g., apomictic versus sexual, and vice versa).

DETAILED DESCRIPTION OF THE INVENTION

Definitions

A promoter is a DNA sequence that directs the transcription of a structural gene. Typically, a promoter is located in the 5' region of a gene, proximal to the transcription start site of a structural gene. If a promoter is an inducible promoter then the rate of transcription increases in response to an inducing agent. In contrast, the rate of transcription is not regulated by an inducing agent if the promoter is a constitutive promoter.

An enhancer is a DNA regulatory element that can increase the efficiency of transcription, regardless of the orientation of the enhancer relative to the start site of transcription.

A silencer is a DNA regulatory element that can decrease the efficiency of transcription, regardless of the orientation of the enhancer relative to the start site of transcription.

The term expression refers to the biosynthesis of a gene product. For example, in the case of a structural gene, expression involves the transcription of the structural gene into messenger RNA and the translation of messenger RNA into one or more polypeptides.

An expression vector is a DNA molecule comprising the regulatory elements necessary for expressing an inserted gene in a host cell. Typically gene expression is placed under the control of certain regulatory elements including constitutive or inducible promoters, tissue-specific regulatory elements, and enhancer elements. Such a gene is said to be "operably linked to" the regulatory elements. Expression vectors typically include eukaryotic and/or bacterial selectable markers that allow for selection of cells containing the expression vector.

An exogenous DNA sequence refers to a DNA sequence that has been introduced into a host cell from an external source. A transgenic plant is a plant having one or more plant cells that contain an exogenous DNA sequence. The term stably transformed refers to a transformed cell or plant that is capable of transmitting an exogenous DNA sequence to its progeny. Typically a stably transformed host has the exogenous DNA sequence integrated into its genome.

A visible marker is defined herein as including any gene that encodes a product that produces a phenotypic trait to the host cell or organism.

A selectable marker is defined herein as including any nucleic acid sequence or gene product that can be selected for after introduction into a cell. The selectable marker facilitates the identification of transformants.

A polylinker is a DNA sequence that contains multiple endonuclease restriction enzyme identification sequences in close proximity of one another.

A blocking sequence or blocking region relates to a nucleotide sequence that when linked to a gene prevents the expression of the gene.

A DNA sequence of interest refers to any DNA sequence that one desires inserted into a plant cell. Typically the DNA sequence of interest encodes for a protein product.

A maintainer plant line is a transgenic plant, regenerated from plant cells transformed with a DNA construct comprising a gene of interest wherein the gene of interest is expressed only upon introduction of site-specific recombinase activity into the cell, and any progeny thereof.

An inducer plant line is a transgenic plant, regenerated from plant cells transformed with a DNA construct comprising a site-specific recombinase gene, and any progeny thereof.

The term F1 relates to the seed or plants produced after multiplication of the original transgenic plants, and more specifically relates to the seed or plants directly produced from the cross fertilization of the maintainer and inducer plant lines. The term F2 relates to the plants or seed directly produced from the F1 plants.

The present invention is directed to the production of a genetically engineered plant having a desired gene that is silent during seed multiplication but is capable of being activated to express its encoded gene product once sufficient numbers of transgenic plants have been generated. In preferred embodiments the gene remains inactive during the growth and multiplication of the original transgenic plant. Preferably, the original transgenic plant (and the resulting progeny thereof) is self fertilized to produce large numbers of plants that are homozygous for the inserted silent gene. Once a sufficient number of plants have been generated the desired gene is expressed in the tissues of the F1 transgenic plants by crossing the multiplied plants with plants that express recombinase activity or by inducing the expression of recombinase activity in the multiplied plants. The F1 seed or F1 plants are then harvested and the gene product is extracted from the plant tissues using standard procedures.

In accordance with one embodiment a first transgenic plant (the maintainer line) is regenerated from plant cells transformed with a DNA construct comprising a DNA sequence of interest wherein the DNA sequence of interest is expressed only upon introduction of site-specific recombinase activity into the cell. In one embodiment the DNA construct comprises a promoter, a blocking sequence, and a structural gene, said blocking sequence being flanked by a pair of site-specific recombination sequences. The structural gene becomes operably linked to the promoter only after the removal of the blocking sequence.

Figure 1A:
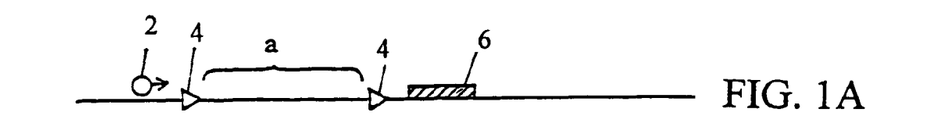
FIGS. 1A-1H are schematic representations of DNA constructs in accordance with this invention.

In one embodiment, shown in FIG. 1A, the site-specific recombination sequences (4) flanking the blocking sequence (a) are orientated relative to one another as direct repeats. In this embodiment, interaction with the respective specific recombinase will result in the deletion of the DNA sequences located between the two repeats (i.e. the blocking sequence) thus operably linking the promoter (2) with the DNA sequence of interest (6).

Figure 1B:
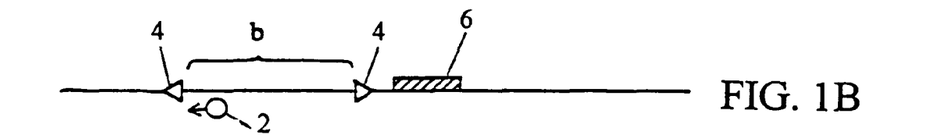

Alternatively, the site-specific recombination sequences (4) flanking the sequences located between the promoter (2) and the DNA sequence of interest can be orientated relative to one another as inverse repeats as shown in FIG. 1B. In this embodiment the DNA sequence of interest (6) and the promoter (2) are not initially operably linked to one another, and the DNA sequence contained in segment "b" is not expressed. However, upon introduction of the appropriate specific recombinase activity, the DNA sequences located between the two repeats will, be inverted, thus operably linking the promoter (2) to the DNA sequence of interest (6). For example, recombinase activity in the hybrid generated by crossing a maintainer line (having the DNA construct of FIG. 1B) with an inducer line (having the DNA construct of FIG. 1D) causes segment "b" to be inverted, thereby operably linking the promoter (2) with the DNA sequence of interest (6) and providing for expression of the DNA sequence of interest (6).

Alternatively, the DNA sequences located between the inverted repeats of the site-specific recombination sequences (4) may include an inverted region of the coding sequence of a gene/DNA sequence of interest, with or without the promoter region. For example, the inverted repeats may be located in separate introns of the gene with the intervening exon being inverted relative to the other gene exons.

The blocking sequence of the present invention comprises a DNA sequence that prevents the transcription or translation of the gene. In one preferred embodiment the blocking sequence comprises an intervening sequence of DNA that physically separates the promoter from the coding sequences of the desired gene. In one embodiment the intervening sequences comprise one or more stop codons that prevent the translation of the corresponding messenger RNA. Alternatively the blocking sequence can be a "silencer" element that suppresses the transcription of the gene. In accordance with these embodiments the blocking sequence is flanked by a pair of directly repeated site-specific recombination sequences such that the introduction of site-specific recombinase activity results in the excision of the blocking sequence and expression of the gene.

Recombinase activity is introduced into the plant cells to excise or invert the blocking sequence, and thus operably link the promoter to the gene, using standard breeding or transformation techniques known to those skilled in the art. Although the site-specific recombination target sequences must be linked to the ends of the blocking sequence, the gene encoding the site-specific recombinase may be located elsewhere. For example, the recombinase gene could already be present in the plant's DNA (under the control of an inducible promoter) or could be supplied by a later introduced DNA fragment either introduced directly into cells, or through cross-pollination. In preferred embodiments a second transgenic plant (the inducer plant line) is utilized to introduce the recombinase activity into the maintainer plant line through cross fertilization. The inducer plant line comprises a multifunctional DNA sequence comprising a site-specific recombinase gene under the control of a constitutive promoter. The multifunctional DNA sequence of the inducer plant can further comprise a selectable marker gene or a visible marker gene. Crossing an inducer plant line with a maintainer plant line will produce F1 progeny that express the desired protein product.

In one preferred embodiment of the present invention, cells of a parent line A, preferably a highly inbred line or variety, are transformed with a first multifunctional DNA sequence comprising a promoter (2), a blocking sequence (a), and a DNA sequence of interest (6). See FIG. 1A. The blocking sequence (a) is flanked by a pair of directly repeated site-specific recombination sequences (4). The DNA sequence of interest (6) is expressed upon introduction of recombinase activity into the cell and removal of the blocking sequence (a). Thus the removal of the blocking sequence (a) operably links the promoter (2) to the DNA sequence of interest (6) and induces the expression of the gene. In preferred embodiments the multifunctional DNA sequence further comprises a visible marker gene or selectable marker gene, and in one embodiment (see FIG. 1C) the blocking sequence further comprises DNA sequences encoding the visible marker gene or the selectable marker gene (8). In another embodiment, the selectable marker gene (8) is located outside the blocking sequence region (a), or alternatively can be located on a separate plasmid and is co-transformed with the multifunctional DNA sequences.

Transformed cells are selected through the use of a selectable marker gene (or alternatively by use of a visible marker), and can be further confirmed by DNA analysis demonstrating the presence of an intact first multifunctional DNA sequence. Fertile plants are regenerated from the transformed plant cells and progeny of the regenerated plants, designated as an A(T) line in the present invention, are maintained and multiplied.

The intervening DNA sequence (blocking sequence "a", see FIG. 1A), prevents the expression of the DNA sequence of interest in A(T) and subsequent generations when selfed or crossed to non-inducer plant lines. Plant A(T) undergoes normal plant and seed development until such time that A(T) is crossed with an Inducer Line "B(T)".

Figures 1C, 1D:
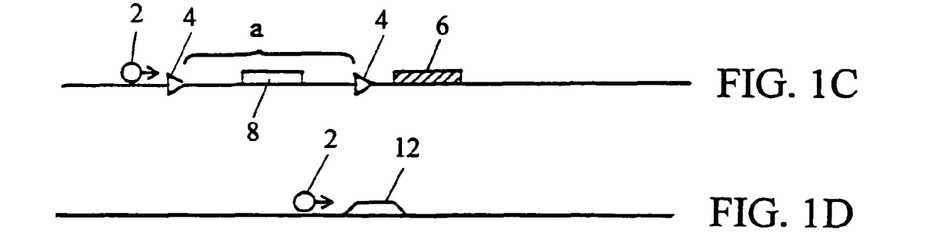

Cells of the parent line B are transformed with a multifunctional DNA sequence comprising a gene that encodes a site-specific recombinase (12), see FIG. 1D to produce inducer line B(T). For example, parent line B can be a highly inbred line or variety that exhibits heterosis when crossed with Maintainer Line A, Transformed cells are selected through the use of a selectable marker gene (or by use of a visible marker), and can be further confirmed by DNA analysis demonstrating the presence of an intact first multifunctional DNA sequence. Fertile plants are regenerated from the transformed plant cells and progeny of the regenerated plants, designated as an B(T) line in the present invention, are maintained and multiplied.

In another embodiment the maintainer line A(T) is crossed as a female to inducer line B(T) as male and F1 seed of A(T)×B(T) is planted and grown to maturity. In the preferred embodiment of the present invention, A(T) is made male-sterile for production of F1 seed by mechanical means or through the use of plant male sterility lines known to those skilled in the art.

In accordance with one embodiment, the maintainer line A(T) is made male-sterile by using a cytoplasmic-genetic male-sterility system. In this embodiment, the male fertile A(T) line is backcrossed at least six times to a cytoplasmic male sterile line, thereby providing a male sterile version, A(T)cms. The male-fertile A(T) line is used as male to maintain the A(T)cms line. In one preferred embodiment the A(T) cms is crossed with B(T) to produce a hybrid plant, where B(T) contains a fertility restoration gene whose presence in the sterile cytoplasm, restores male fertility.

Figure 1E:
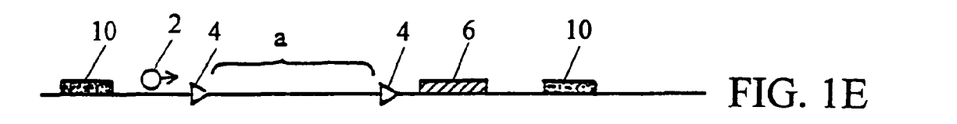

In another embodiment, the maintainer line A(T) is made male-sterile by a transgenic hybrid production system. In this embodiment, the blocking sequence (a) as shown in FIG. 1G comprises DNA sequences that encode a selectable marker gene (8), such as a constitutively expressed herbicide resistance gene, and a suicide gene (16) that is operably linked to an anther specific promoter, wherein expression of the suicide gene product prevents pollen grain development. Alternatively, a visible marker gene can be used in place of the selectable marker gene. Regenerated plants of Parent line A(T) containing this male sterility system [A(T)tms plants] are sib-pollinated by transformed or untransformed A plants. One-half of the progeny from this cross will be male-fertile, herbicide-susceptible and one-half will be male-sterile, herbicide-resistant. The progeny from such crosses are treated with herbicide and male-fertile plants are destroyed.

The resistant male-sterile plants are again sib-pollinated by A plants. This process is repeated to maintain the A(T)tms line and to produce the line in quantities required for commercial use. A(T)tms×A plants are treated with herbicide in a hybrid seed production field and pollinated by B(T) plants. The recombinase gene from B(T) is active in the resulting zygote formed from the cross fertilization of A(T)tms×B(T) plants and in all cells during development of the A(T)tms×B (T) F1 plant. The recombinase excises the blocking sequence (a), including the selectable marker gene (8) and the suicide gene (16) thereby restoring male fertility and placing the promoter (2) in operable connection with the DNA sequence of interest (6), see FIG. 1G. Thus the DNA sequence of interest (6) is expressed, under control of the promoter (2), in the developing F1 grain. Expression of the DNA sequence of interest in the developing F1 plant will depend on the selectivity of the gene promoter. If the promoter is a constitutive promoter, then the DNA sequence of interest will be expressed in the F1 grain (zygote). If the promoter is a tissue specific or developmentally regulated promoter, expression may be further regulated. For example if the promoter is a seed specific promoter, then the gene product will not be expressed until the F2 seed is produced.

Expression of the desired gene product can be delayed indefinitely in the maintainer line, therefore, and the expression is not induced until recombinase activity is introduced into the plant, for example by cross fertilizing the maintainer line is with an inducer line. In one embodiment the cross fertilized parent lines (A and B) are identical, and the gene of interest expressed in the F1 plants (generated by crossing maintainer line A(T) with inducer line B(T), i.e. parent lines A and B transformed with the DNA constructs necessary for creating the maintainer and inducer lines) is used to produce a female parent for the commercial production of hybrid seed. For example, in one embodiment the F1 plants (A(T)×B(T)) are male sterile and are crossed with plant line C, where parent line C is a highly inbred line or variety that exhibits heterosis when crossed with parent line A and where parent line C is capable of restoring fertility to the resulting hybrid plants.

In one embodiment, the inducer plant comprises a DNA construct encoding a site-specific recombinase gene (12) that is operably linked to a constitutive promoter (see FIG. 1D). The DNA construct of the inducer plant may also include a visible or selectable marker gene. The maintainer plant comprises a DNA sequence comprising a DNA sequence of interest, a blocking sequence and an inducible or tissue specific promoter, wherein the blocking sequence is flanked by a pair of site specific recombinase sequences and is located between the promoter and the DNA sequence of interest (See FIG. 1A). The DNA construct of the inducer plant may also include a visible or selectable marker gene. In one embodiment the visible or selectable marker gene is located between the pair of site specific recombinase sequences. Upon cross fertilization of the inducer and maintainer lines, the recombinase gene is expressed in the zygote of the A(T)×B(T) F1 plant and removes the blocking sequence. Upon removal of the blocking sequence the DNA sequence of interest becomes operably linked to the inducible or tissue specific promoter and the gene product is expressed upon contact with an inducer or in a tissue specific manner in the F1 plants.

In one preferred embodiment the inducer plant line comprises a DNA construct of FIG. 1D, and the maintainer plant line comprises the DNA construct of FIG. 1A or 1C, wherein the promoter (2) used to express the DNA sequence of interest (6) is a seed specific promoter that only expresses its linked gene product in the seeds of the plant. For example, one seed specific promoter in accordance with the present invention is a promoter that expresses its operably linked gene only in the endosperm of the seed. In accordance with this embodiment, after cross fertilizing the inducer line with the maintainer line the blocking sequence is removed, but the DNA sequence of interest is expressed only occurs within in the developing F1 grain. Thus the DNA sequence of interest (6) is activated only during the last generation of seed production, i.e. during the commercial seed production stage and not during multiplication of the maintainer and inducer plant lines. The seeds are then harvested using standard harvesting techniques and equipment, and the desired product is extracted from the seeds. In this embodiment, F1 seeds, i.e. those produced immediately after crossing the maintainer and inducer plant lines, contain the desired gene in its activated form. Since large numbers of transgenic plants are produced during the multiplication step, any loss of seed viability and germination is of little consequence with respect to the production of the compound in question.

Alternatively the promoter of the gene of interest can be a leaf specific promoter that only expresses its linked gene product in the leaf of the plant (for example, the gene is expressed only in the leaf blades of a cereal or grass). In this embodiment, the product can be harvested from the leaves of the F1 plant, including, for example, grass clippings of the F1 plant.

Alternatively, the recombinase gene of the inducer plant line can be operably linked to a tissue specific promoter or an inducible promoter. In this embodiment the recombinase gene is only expressed in the F1 progeny after contact with an inducer, or is expressed only in certain tissues. Only those cells that express the recombinase gene will activate the expression of the gene of interest in the progeny of a cross between an inducer line and a maintainer line, wherein the maintainer line comprises a DNA construct of FIG. 1A or 1C. For example, the promoter of the recombinase gene can be a seed specific promoter and thus the recombinase gene is only expressed in the developing seed of the F1 plant. Thus recombinase activity is limited to the F1 grain of the progeny of the cross between the maintainer and inducer plant lines and the desired gene product is expressed only in the F1 grain. The F1 grain is harvested and processed to extract, isolate, purify and otherwise process a product resulting from the expression of the DNA sequence of interest.

One skilled in the art of molecular biology and plant breeding will recognize additional means of practicing the present invention. For example the multifunctional DNA sequence that encodes the desired gene can be further provided with DNA sequences that share homology to sequences endogenous to host plant. In particular the multifunctional DNA sequence may comprise two homologous DNA sequences (10) that flank the sequences targeted for insertion into the host plant's DNA (See FIG. 1E). The homologous DNA regions foster insertion of the flanked sequence into the plant cell's DNA via a homologous recombination event, thus allowing the insertion of the sequence to a specific predetermined target of the plant cell's DNA. In one embodiment, a visible or selectable marker gene is located between the pair of site specific recombinase sequences. In a further embodiment, as shown in FIG. 1H, a first visible or selectable marker gene (18) is located between the pair of site-specific recombinase sequences (4) and a second visible or selectable marker gene (20) is located outside the region flanked by the pair of site-specific recombinase sequences (4), but within the region flanked by the homologous DNA sequences (10). Preferably the first and second visible or selectable marker gene are different from one another, thus allowing for identification of the original transformed plant B(T) containing the construct of FIG. 1H, and subsequent identification of the generated hybrid plants A(T)×B(T) that have the blocking sequence removed, but retain the remaining elements of the DNA construct. In one embodiment the first visible or selectable marker gene (18) is a visible marker gene and the second visible or selectable marker gene (20) is a selectable marker gene such as an herbicide resistance gene.

Figure 1F:
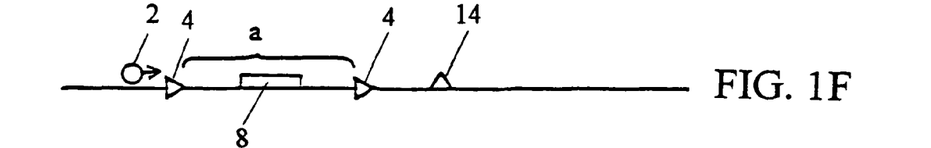
Figure 1G:
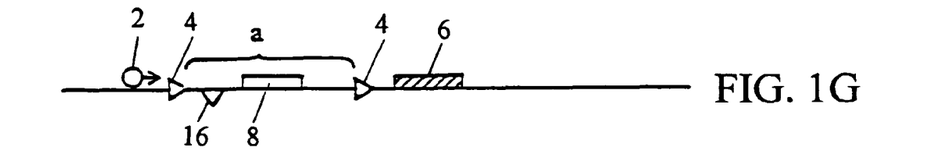
Figure 1H:
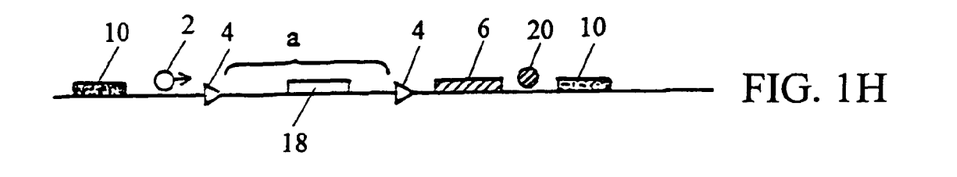

The multifunctional DNA sequence used to produce the transgenic plants of the present invention may include sequences encoding a selectable marker gene (8) or a polylinker region (14), see FIG. 1F. A polylinker is a short length of DNA that contains numerous different endonuclease restrictions sites located in close proximity. The presence of the polylinker is advantageous because it allows various expression cassettes to be easily inserted and removed, thus simplifying the process of making a construct containing a particular DNA fragment. In accordance with the present invention a DNA construct can be prepared comprising the genetic elements of the constructs of FIG. 1A, 1B, 1E, 1G or 1H, wherein the DNA sequence of interest (6) comprises a polylinker region as shown in FIG. 1F.

The above described transformation construct can also be part of a larger construct. The additional sequences of the larger construct comprising DNA sequences capable of replicating the entire DNA molecule in a bacterial host and DNA sequences encoding a bacterial selectable marker (such as genes encoding for ampicillin or tetracycline resistance). This larger construct, ideally a plasmid, can be used to transform bacterial cells. These transformed bacterial cells can then be cultured to produce large quantities of the plasmid DNA. The specific transformation construct can then be isolated using techniques well known to those familiar with the art.

In one embodiment, as shown in FIG. 1A, a multifunctional DNA sequence for use in transforming eukaryotic cells comprises a promoter (2), a DNA sequence of interest (6) encoding a deleterious but commercially valuable product and a blocking sequence (a) wherein the blocking sequence is flanked by two directly repeated site-specific recombination sequences (4). In one embodiment the blocking sequence includes a gene encoding a selectable marker (8), see FIG. 1C. The multifunctional DNA sequence can be flanked on each end by nucleotide sequences sharing homology to nucleotide sequences present in the eukaryotic cell to be transformed to target the insertion of the multifunctional DNA sequence to a predetermined locus of the host cell's DNA (see FIG. 1E).

In another embodiment of the present invention a multifunctional DNA sequence for use in transforming eukaryotic cells comprises a promoter (2), a polylinker region (14) and a blocking sequence (a) wherein the blocking sequence is flanked by two directly repeated site-specific recombination sequences (4), see FIG. 1F). In preferred embodiments the blocking sequence is positioned between the promoter and the polylinker region. The polylinker region allows for the ease of insertion of a DNA sequence of interest into the multifunctional DNA sequence. After insertion of the DNA sequence of interest the DNA construct is used to transform plant cells to generate various maintainer plant lines.

Example 1

FLP Mediated Site-Specific Recombination Between Plasmid FRT Sites in Maize and Rice Cells Materials and Methods
Synthesis of FLP Expression Vectors
Plasmid constructions. A 6.8 kb Bam HI-XhoI fragment of maize genomic DNA containing the adh1-S gene was inserted into the BamHI-SacI sites of pBR322 to yield pBx26. A control vector pAeiGUS, was constructed by replacing the PvuII fragment of pBx26 (containing most adh1 coding sequences) with a SmaI-EcoRI fragment containing the gusA coding sequence and a nos polyA site. Thus, the construction contains a 1.5 kb BamHI-PvuII fragment from the adh1 genomic clone with the first exon and intron A of the adh1 gene fused in-frame to the gusA coding sequence; however, the gusA coding sequence still has its own start codon intact. Plasmid pAHC27 was provided by Dr. Peter Quail, University of California, Berkeley. Plasmids pNEOβGAL and pOG44 were purchased from Stratagene, LaJolla, Calif. pUbiGUS was constructed by ligating the maize ubiquitin gene 5' controlling elements in front of the gusA coding sequence by ligation of the XbaI fragment of pAHC27 into HindIII-BamHI restriction sites of p35SGUS. For the construction of pAeiFLP, both pAeiGUS and pOG44 were digested with BglII and SacI. The 1.5 kb fragment carrying the FLP coding sequence from pOG44 was then ligated directly into the eluted 4.4 kb fragment of pAeiGUS replacing the gusA coding sequence. pUbiFLP was obtained by isolating the 1.5 kb SacI-HindIII FLP fragment from pOG44 and subcloning into the respective sites of pGEM-7Z(−)f (Promega, Madison, Wis.)). The resulting plasmid was cleaved with SacI and SmaI, and the 1.5 kb FLP fragment was then ligated directly into SacI-SmaI digested pUbiGUS replacing the gusA fragment with the FLP gene.

Synthesis of FRT Containing Vectors
Two Primers
(5'-GTGATCAGAAGTTCCTATTCCGAAGTTC-CTATTCTCTAGAAA-3' (SEQ ID NO:1)) and (5'-CTGAT-CAGAAGTTCCTATACTTTCTAGA-3' (SEQ ID NO:2)) were annealed (4 nmoles each) and incubated with 5 units of T4 DNA polymerase and 60 nmoles of each dNTP in 0.1 ml at 11° C. for 3 hrs. to form a complete FRT recombination site of 48 bp. The primer-extended fragments contained a BclI restriction site on each end. Phosphate groups were then added to the terminal nucleotides by incubation with 20 units of T4 DNA kinase and 16 nmoles ATP in 30 µl of 1× kinase buffer. The resulting double-stranded DNA fragments were blunt-end ligated and cleaved with BglII restriction enzyme. The products were then ligated directly into the BglII site of pUbiGUS forming pUFRTG. For the construction of the pUFRTmG vector, containing a minimal version of the FRT site (37 bp), the primer extended products were blunt-end ligated into the BglII site of pUbiGUS (the BglII site of pUbiGUS was filled-in using T4 DNA polymerase). Confirmation of the minimal FRT sequence was done by sequencing the double-stranded plasmid DNA. pU2FRTG and pU2FRTmG were constructed by ligation of the 1.3 kb XbaI fragment of pNEOBGAL into pUFRTG and pUFRTmG, respectively. The test plasmid pUbiFRT for intermolecular recombination was constructed by EcoR1 restriction of pU2FRTmG and religation of the resulting plasmid DNA fragments. The other substrate for intermolecular recombination, pFRTGUS, was obtained by digestion of pU2FRTmG with EcoRI and BamHI, isolation of the fragment containing the gusA coding sequence and the FRT site, and ligation of the resulting fragment into the respective sites of pGEM-7Z(−)f (Promega, Madison, Wis.).

Molecular Analysis of DNA
Polymerase chain reactions (PCRs) were carried out in a Perkin-Elmer Cetus DNA thermal cycler. Amplification was performed using reagents and protocols as outlined by the Perkin-Elmer Cetus GeneAmp PCR Kit (Perkin-Elmer Cetus, Norwalk, Conn.). Sequences of primers were as follows: 5'-CCCCAACCTCGTG-3'(SEQ ID NO:3) for the first exon of the ubiquitin gene and 5'-GGGGTTTCTACAG-GACG-3' (SEQ ID NO:4) for the 5' end of the gusA coding sequence. PCR reactions contained: 5 µl of template DNA, 5 µl of primer solution (50 nmoles each), 5 µl of 10×PCR buffer II (22), 2.0 µl dNTPs mix (final concentration 200 µM of each nucleotide), and 0.25 µl of Taq polymerase (2.5 units/100 µl) in a final volume of 50 µl. Denaturation, annealing, and extension steps were performed at 94° C. for 1 minute, 45° C. for 1 minute, and 72° C. for 2 minutes, respectively. The extension steps were increased 15 seconds with each cycle. Five microliters of each amplified product were analyzed using 1.0% agarose gel electrophoresis.

Southern blotting of agarose gels containing PCR amplified DNA was performed using capillary transfer to Hybond-N membrane (Amersham, Arlington Heights, Ill.). DNA was fixed to the membrane by UV irradiation and incubated in prehybridization solution (5×SSPE, 5×Denhardt's solution, 0.5% SDS) at 65° C. for 4 hours. The radioactive probe (α $^{32}$P-labeled SmaI-BgglII fragment isolated from pUbiGUS) was prepared using the Multiprime DNA labeling system according to the manufacturer's instructions (Amersham, Arlington Heights, Ill.). The probe contained the complete ubiquitin intron and part of the first exon. The blot was hybridized overnight in prehybridization solution at 65° C. and subsequently processed according to standard procedures.

The nucleotide sequences of the FRT sites were determined by a modified dideoxy method using Sequenase Version 2.0 (United States Biochemical Cleveland, Ohio). CsCl purified pUFRTG and pU2FRTmG plasmid DNA was used as template DNA. The primer used was the same as that used for PCR which annealed to the 5' end of the first exon of the ubiquitin gene.

Transformation Procedures

The cell suspension culture of maize (Zea mays L.) was initiated from A188×BMS type II callus and maintained (Kamo et al. 1987, Planta, 172, 245-251). Seven days prior to protoplast isolation, 2 ml packed cell volume (PCV) of the suspension culture was transferred into 37 ml of MS medium (Murashige et al., 1962, Physiol Plant, 15, 473-497) supplemented with 3.5 mg/l 2,4-D.

Approximately 5 ml PCV of suspension cells were digested for 3 h in 20 ml MS medium containing 0.2M mannitol, 0.5 mg/l thiamine, 2 mg/l 2,4-D, 80 mM $CaCl_2.2H_2O$, 2% cellulase, 0.25% pectinase, and 0.1% pectolyase Y-23, pH 6.0 Protoplasts were filtered through a 48 μm nylon mesh screen and pelleted by centrifugation at 50×g for 15 minutes. The pellet was suspended in 8 ml of protoplast culture medium (PCM containing 9% Ficoll 400 and overlaid with 4 ml of transformation medium (TM). The transformation medium consisted of 100 mM MES buffer, pH 5.5, 0.2 M mannitol, and 80 mM $CaCl_2.H_2$. Following centrifugation at 75×g for 10 minutes, a band of protoplasts was collected from the interphase, and the concentration was adjusted to $1.0 \times 10^7$ protoplasts/ml with TM.

Protoplast transformation was performed in 12 ml Falcon polystyrene tubes by pipetting 20-25 μl of plasmid DNA (1.0 mg/ml) followed by 0.5 ml of protoplasts and 0.5 ml of 50% PEG (polyethylene glycol, MW=8000; dissolved in F-solution. Protoplasts were incubated for 20 minutes at room temperature. After incubation, 330 μl of the protoplast solution was transferred to a 12-well microculture dish containing 2 ml solidified 0.8% low melting point agarose in PCM. Plates were then wrapped with Parafilm and incubated at 25° C. in the dark for approximately 24 hours.

GUS Activity and Protein Determination

Following the 24 hrs. incubation, protoplasts were collected and resuspended in 300 μl of GUS extraction buffer containing 0.1% Triton X-100. After centrifugation at 16,000×g for 5 minutes, a 25 μl extract of the protoplasts was incubated with 150 μl of 1 mM MUG (4-methyl umbelliferyl β-D-glucuronide) in GUS extraction buffer in a 96-well plate at 37° C. Reactions were stopped at various times by adding 125 μl of GUS stop buffer (0.2 M $CaCO_3$). Fluorescence (excitation at 362λ and emission at 455λ) was measured in a Perkin Elmer Luminescence Spectrometer LS50B calibrated with standards of methyumbelliferone. GUS activity was calculated from the slope of the line generated from time points and normalized to the protein content determined by the method of Bradford, 1976, Anal. Biochem., 22, 248-254.

Results

The FLP/FRT site-specific recombination system used in these studies consists of two elements: plasmid DNA encoding for the FLP enzyme and test plasmids containing the FRT recombination sites.

The target FRT nucleotide sequence consists of three recreated DNA sequences of 13 bp each; two repeats in a direct orientation and one repeat inverted relative to the other two. In addition, there is an 8 bp spacer region between the repeats which determines the orientation of the FRT recombination site and which serves as the site of sequence pairing that initiates the recombination event. The FLP recombinase binds to all three repeats, anneals DNA sequences within spacer regions of two FRT sites, cleaves the sites at the borders of the spacer, and exchanges the DNA strands. Depending on the orientation of the recombination sites, the DNA fragment between the FRTs can be either inverted or excised. Additionally, the FLP recombinase can act on target FRT sites located on separate DNA molecules. These intermolecular recombinations can lead to integration of foreign DNA into FRT sites in bacterial and mouse genomes.

Figure 2:
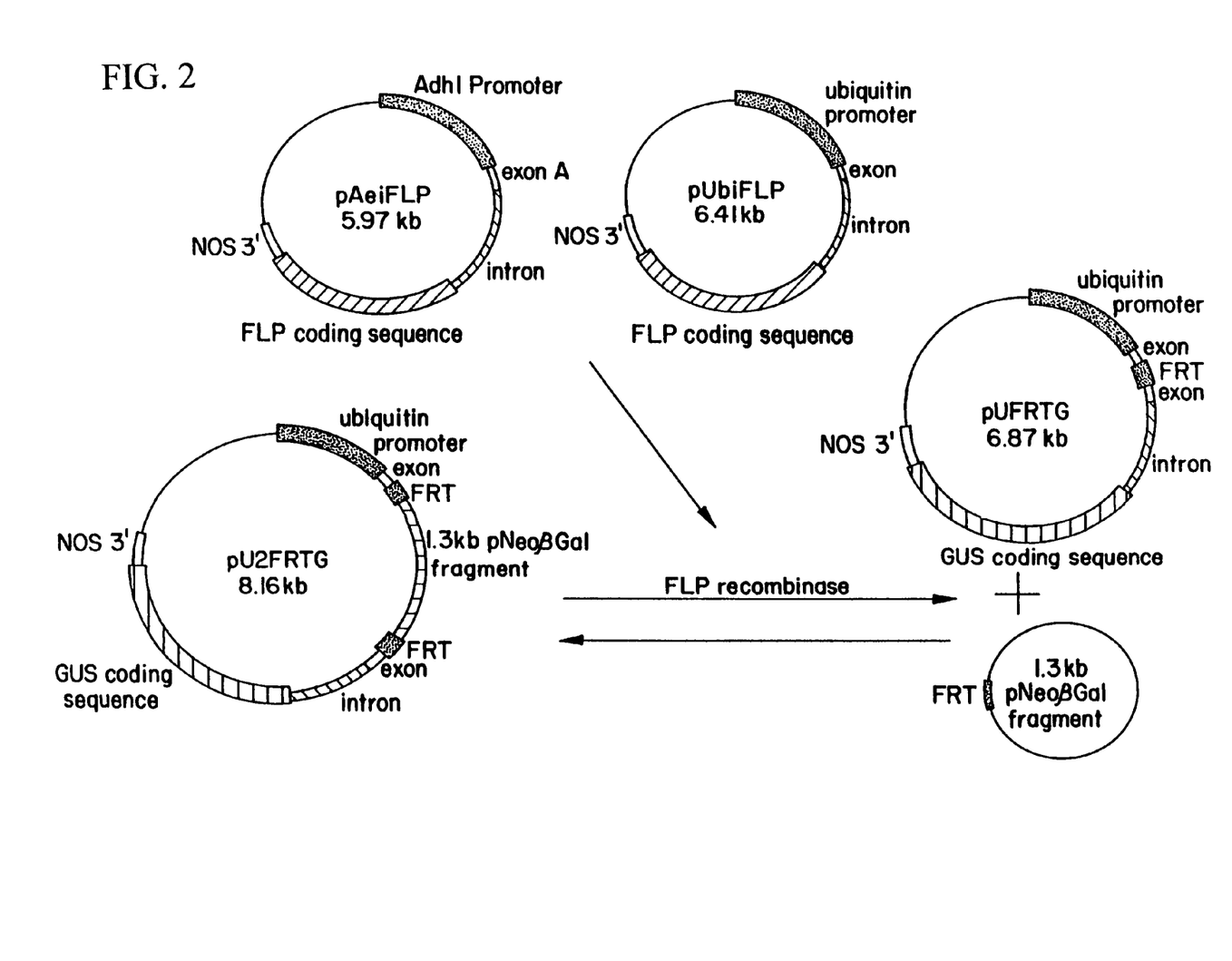
FIG. 2 is a diagrammatic representations of FLP expression vectors used to study activity of yeast FLP/FRT system in plant protoplasts.
Figure 3:
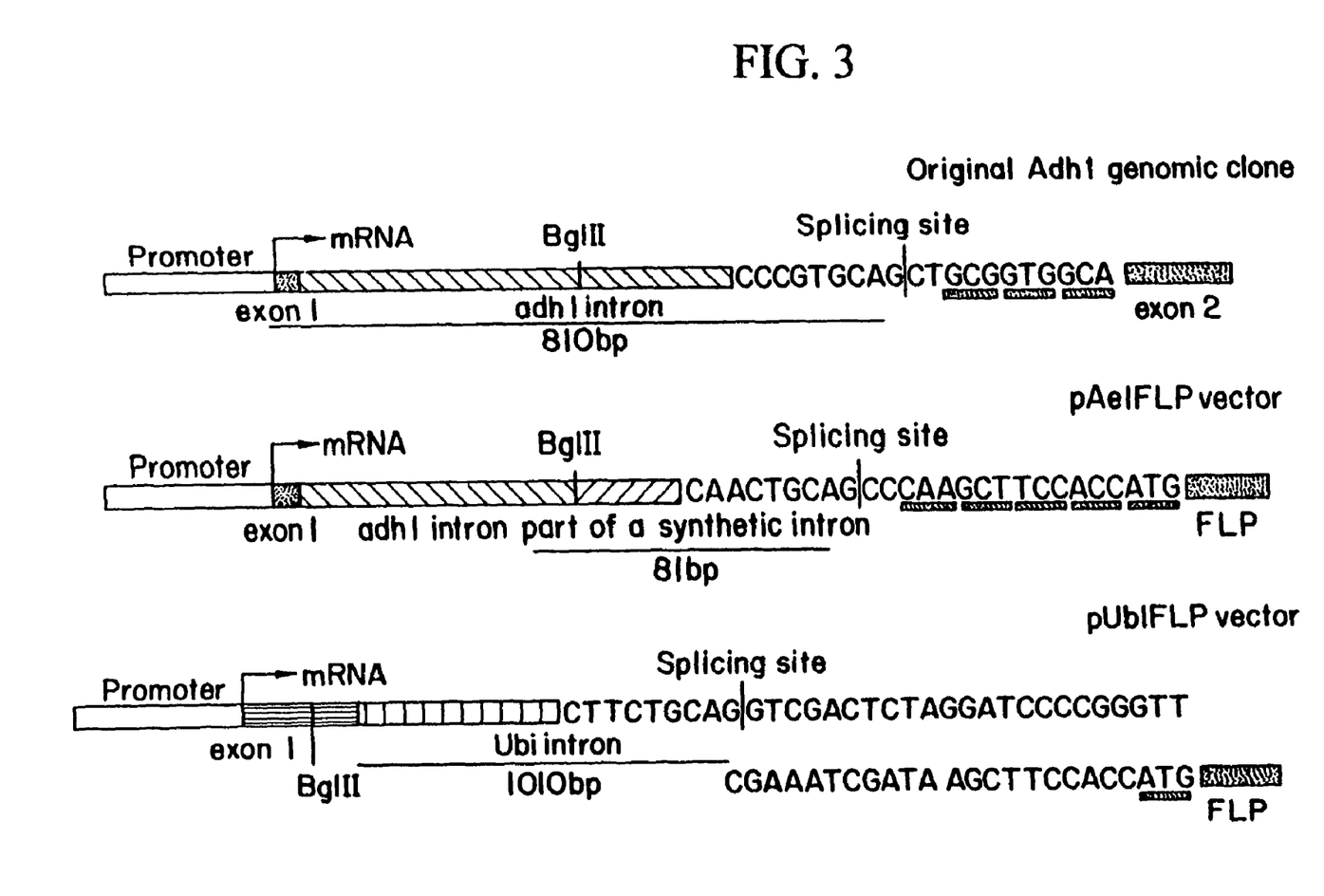
FIG. 3 is a diagrammatic representations of FLP expression vectors used to study activity of yeast FLP/FRT system in plant protoplasts.

FIGS. 2 and 3 illustrate the strategy and diagram of the FLP expression vectors used to study activity of yeast FLP/FRT system in plant protoplasts. More particularly FIG. 2 shows components of the recombination system to test the DNA excision reaction catalyzed by the FLP protein. FLP enzyme can be produced by either pAeiFLP or pUbiFLP. FIG. 3 shows the sequence of the splicing site of the original adh1 genomic clone (SEQ ID NO:5) and the sequence of the junction sites between cloned FLP coding sequence and adh1 (SEQ ID NO:6) or ubiquitin maize (SEQ ID NO:7) promoters. Thick lines indicate an open reading frame of adh1 gene or the translation start codon for FLP protein synthesis in the pUbiFLP vector. Note that the first exon of the maize ubiquitin gene in contrast to the adh1 first exon is not translated.

Figure 4A:
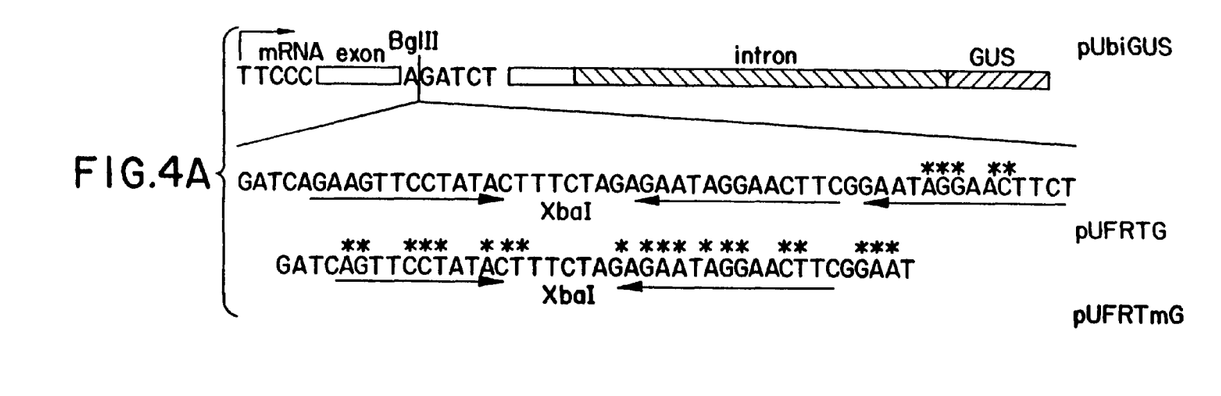
FIGS. 4A and 4B illustrate the structure of the FRT site-containing vectors.

FIG. 4A illustrates the structure of the FRT site-containing vectors. A single complete (SEQ ID NO:8) or partial (SEQ ID NO:9) FRT site was ligated into the BglII site of the ubiquitin first exon. Asterisks show the FLP binding sites. Arrows denote 13 bp inverted repeats. pUFRTmG vector contained only one 13 bp repeat and one shorter 11 bp inverted repeat. This FRT site lacks additional five FLP protein binding sites. Insertion of the XbaI the fragment of pNEOβGAL into the XbaI site of the FRT vectors provided the second FRT site and led to inactivation of GUS expression.

The FLP recombinase expressed from FLP vectors should recombine test plasmid DNA within the FRT target sites to restore expression of GUS enzyme. Expression of the FLP gene was driven by the maize adh1 promoter in pAeiFLP and by the maize ubiquitin promoter in pUbiFLP (FIG. 3). Both constructs included the first exon and intron of the respective genes. In the pAeiFLP construction, the first intron contained 290 bp of the first adh1 intron fused at the BglII site to 81 bp of the synthetic intron from pOG44. Both promoters proved to be very effective as determined in transient GUS expression assays of maize protoplasts; however, the ubiquitin promoter was superior.

The BglII site of the first exon of the ubiquitin promoter in pUbiGUS was chosen for insertion of the FRT sequences following initial screening of other appropriate insertion sites. Two different FRT sites were ligated into the BglII site—one minimal 37 bp FRT site referred to as FRTm and one complete 48 bp FRT site referred to as FRT (FIG. 4A). The FRTm site lacks the third repeat which includes five additional FLP protein binding sites; however, a similar FRT deletion (missing one repeat and the same FLP protein binding sites) has been shown to be as effective as the wild-type FRT site in vitro. Interestingly, insertion of the FRTm site into the pUbiGUS resulted in higher expression of the GUS enzyme. Insertion of the full length FRT site resulted in reduction of GUS expression.

Figure 4B:
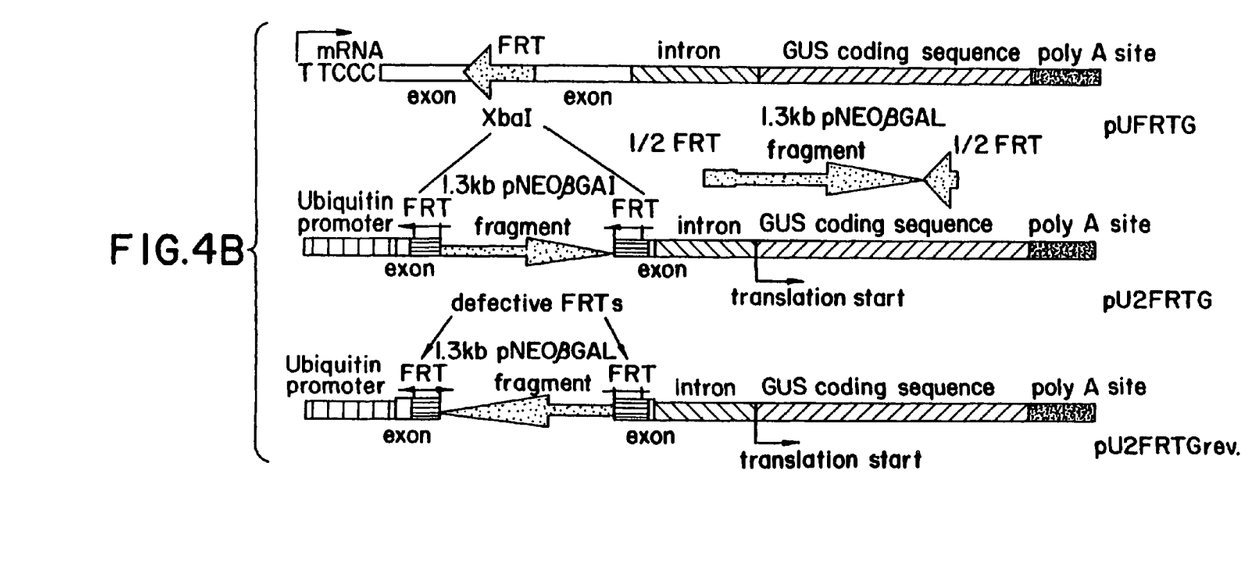

A second FRT site for intramolecular recombination of test plasmids was created by insertion of the MaI fragment of pNEOPGAL into the single XI site of pUFRTG. Insertion of the pNEOPGAL fragment provided supplemental sequences to form an additional FRT site and a 1.31 kb spacer DNA which separated the ubiquitin promoter from the gusA coding sequence (FIG. 4B). As a result, GUS activity in maize protoplasts transformed with pU2FRTG was substantially reduced. The reverse orientation of the ligated XbaI fragment of pNEOβGAL should also inactivate GUS expression but should not form functional FRT sites. pU2FRTmG rev. and pU2FRTG rev. vectors (FIG. 4B) were used to demonstrate that fully functional FRT sites were required to obtain activation of GUS expression by the FLP protein.

Transient GUS activity in maize protoplasts co-transformed with pAeiFLP and pU2FRTmG was higher than in protoplasts transformed with only pU2FRTmG. The restored GUS expression was approximately 10% of that observed after protoplast transformation with the control pUFRTmG. GUS activity in maize protoplasts transformed with pAeiFLP was similar to background GUS activity. Thus, the FLP/FRT recombination system appeared to function in maize protoplasts. This was further substantiated by the increase of GUS activity in maize protoplasts co-transformed with increasing amounts of pAeiFLP DNA. This indicated not only that GUS expression is dependent on the amount of the FLP enzyme present, but also that the amount of the FLP protein might have been the limiting factor in the recombination process. When pUbiFLP was introduced into maize protoplasts along with the test plasmids, GUS activities were restored for both pU2FRTmG and pU2FRTG to 81% and 45% of the respective control treatments. Reactivation of GUS in the presence of pUbiFLP and the vectors containing both FRT's indicated that FLP protein catalyzed excision of the 1.31 kb fragment. When the FRT's were mutated by the reverse ligation of the 1.31 kb fragment (pU2FRTmG rev. and pU2FRTG rev.), GUS activity was not restored indicating that these FRT sites were not recognized by the FLP protein.

To observe intermolecular recombination at the FRT sites, the ubiquitin promoter or the gusA coding sequence was removed from pUFRTmG to form pUbiFRT and pFRTGUS, respectively. Introduction of two different FRT sites into protoplasts on two separate DNA molecules (pUbiFRT and pFRTGUS) produced approximately a 4-fold increase in GUS activity above background activity in protoplasts transformed with pFRTGUS alone. This activity was 15% of the positive control (protoplasts transformed with pUFRTmG). The relatively high background expression of GUS in pFRTGUS transformed protoplasts (6±1 unit) might be the result of the entire first intron and part of the ubiquitin first exon being present in this vector.

The FLP/FRT recombination system has also been tested in rice protoplasts. The recombinase-mediated excision of DNA proved to be as effective in rice as in maize protoplasts. The same pattern of response was observed for the different plasmid constructions containing FRTs. Co-transformation of rice protoplasts with pUbiFLP and either pU2FRTmG or pU2FRTG gave 75% and 31% restoration of the control GUS activity. Vectors containing inactive FRT sites gave only 1-2% of the control GUS activity.

PCR analysis of total DNA isolated from co-transformed maize protoplasts indicated the presence of recombinant plasmid DNA molecules. The two primers used for this analysis amplify the region between the ubiquitin transcription start and the 5' end of the gusA coding sequence. The length of this region is 2.49 kb in pU2FRTGm and pU2FRTG. After removal of the 1.31 kb fragment as a result of the recombination reaction, the amplified region should be reduced to 1.18 kb and should then be equivalent to the amplification product of pUFRTG DNA. A 1.18 kb fragment was identified in the products of the PCR reaction using total DNA isolated from maize protoplasts co-transformed with pU2FRTmG and pUbiFLP as a template. The identity of this fragment was confirmed through hybridization using a probe specific to the first intron of the ubiquitin gene.

Discussion

The results presented here show that the FLP recombinase of yeast can promote the site-specific recombination between FRT sites in both maize and rice cells. This conclusion is based on the following evidence. Transient expression of the GUS enzyme from recombination test vectors increased in protoplasts co-transformed with functional FLP expression vectors, and the magnitude of this increase depended on the amount of co-transformed plasmid DNA containing the FLP gene. Additionally, higher expression of GUS protein in co-transformed protoplasts was observed when a stronger promoter was used to drive expression of the FLP protein. The increase in GUS expression was abolished if the FRT sites in test vectors were mutated. Lastly, the products of the site-specific recombination reaction were identified in co-transformed protoplasts.

Example 2

Excisional Recombination

The pU2FRTGUS DNA construct, containing a 1.3 kb DNA fragment with a unique BamHI restriction site located between the two FRT sites was utilized in a series of excisional recombination experiments. The BamHI restriction site allows for the insertion of additional DNA sequences to increase the distance between the two FRT sites. The efficiency of the excision reaction, relative to the distance between the two FRT sites, is evaluated using the transient GUS expression assay.

Two different methods can be used to evaluate the efficiency of the FLP recombinase in the excision of integrated foreign genes: retransformation and controlled expression of the recombinase gene.

Re-Transformation

Figure 5:
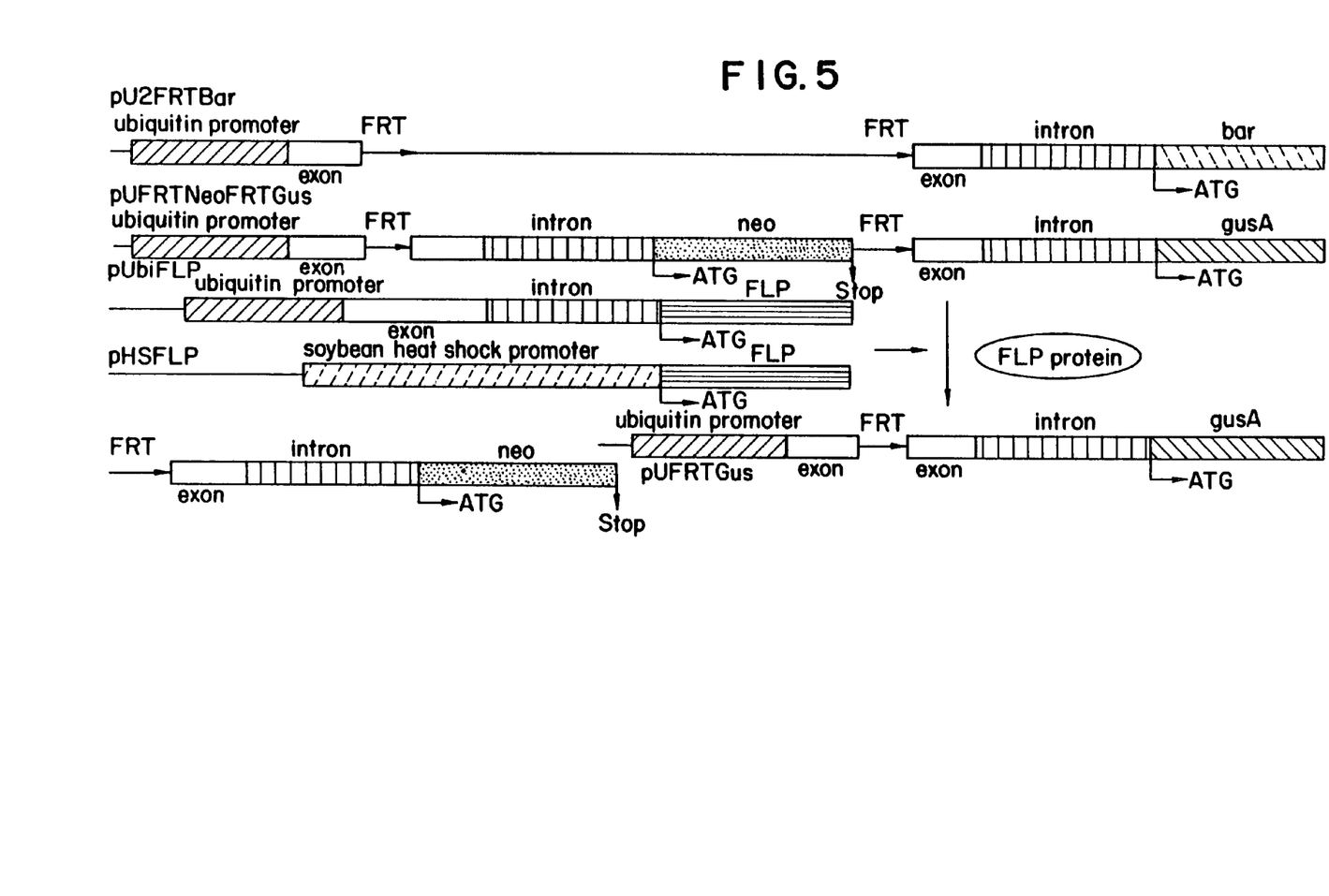
FIG. 5 provides diagrams of vectors for testing excisional recombination.

In the first method, maize protoplasts are transformed with a DNA construct containing the gusA gene inactivated by insertion of the neo gene into the promoter region of the gusA gene (pUFRTNeoFRTgus). The neo gene is positioned between two directly-repeated FRT sites and is expressed (FIG. 5).

Selection of transformed protoplasts on medium with kanamycin results in transgenic calli with a neo+gus– phenotype. These calli serve as initial material to establish new suspension cultures. Protoplasts isolated from these suspension cultures and re-transformed with the pUbiFLP DNA construct excise the neo gene and thus yield gus+ phenotypes, which can be detected in transient assays. These relatively simple experiments provide information about the existence of the excision reaction catalyzed by the FLP protein in plant cells.

Controlled Expression of the FLP Gene

In the second approach, expression of the FLP gene is controlled to achieve excision so as to eliminate the re-transformation step in favor of controlling the FLP recombinase activity. Maize protoplasts are with the pUFRTNeoFRTGus plasmid DNA and plasmid constructions containing the FLP gene under control of the soybean heat shock inducible promoter. Studies of the activity of the soybean Gmhsp 17.5-E gene promoter in maize protoplasts and cells showed excellent performance of this promoter in response to heat shock treatment. The background activity at 24° C. was low and a several fold increase of activity was observed after heat shock at 42° C. for 0.5-1 hour. The DNA construct containing the FLP gene under the control of this heat shock promoter was made (pHSFLP) and tested in transient assays for site-specific recombination (Table 1).

TABLE 1

| Vector used for transformation | GUS activity nmol MU/min/mg protein Heat shock (hrs) | | | GUS activity corrected for pU2FRTmG background Heat shock (hrs) | | | GUS activity corrected for pUFRTmG expression Heat shock (hrs) | | | GUS activity corrected for pUbiFLP expression Heat shock (hrs) | | |
|---|---|---|---|---|---|---|---|---|---|---|---|---|
| | 0 | 0.5 | 1 | 0 | 0.5 | 1 | 0 | 0.5 | 1 | 0 | 0.5 | 1 |
| -DNA | 0.06 | | | | | | | | | | | |
| pUFRTmG | 58 | 41 | 41 | 58 | 41 | 41 | 58 | 58 | 58 | 58 | 58 | 58 |
| pU2FRTmG | 0.6 | 0.6 | 0.4 | 0 | 0 | 0 | 0 | 0 | 0 | 0 | 0 | 0 |
| + pUbiFLP | 58 | 33 | 20 | 58 | 33 | 20 | 58 | 47 | 28 | 58 | 58 | 58 |
| + pHSFLP | 0.8 | 8.4 | 9.1 | 0.2 | 7.8 | 8.7 | 0.2 | 11.1 | 12.4 | 0.2 | 14.0 | 24.8 |

There still remains the possibility that the residual FLP activity at room temperature might be too high, which could lead to excision reactions prior to the heat shock treatment. Modifications to the transformation procedure are made as necessary, such as growing the transformed protoplasts and cells at lower temperatures.

Once stably transformed calli are selected on medium containing kanamycin, the heat shock treatment activates the FLP gene leading to the excision of the neo gene and activation of the gusA gene. Three different phenotypes are generated: neo+gus−, neo+gus+, neo-gus+. The relative frequency of these phenotypes in relation to the copy number of integrated plasmid molecules provides an estimate of the efficiency of the excision reaction.

Example 3

*Arabidopsis thahana* plants have been transformed with *Agrobacterium tumefaciens* containing binary vectors with the following gene sequences:
1. CaMV35S promoter, FRT, neo-resistance gene, FRT, gusA; a first multifunctional DNA sequence
2. CaMV35S promoter, neo-resistance gene, CaMV35S promoter FLP; a second multifunctional DNA sequence Plants were transformed with *Agrobacterium* containing constructs 1 or 2. Seeds were grown on kanomycin and putative transformants were selected. The plants were allowed to self pollinate, and again seeds were grown on kanomycin to select putative transformants. This cycle was repeated to the T3 generation and homozygous lines were obtained based on segregation for kanomycin-resistance. The plants were confirmed to be transformed by Southern blotting. Plants homozygous for construct I did not express gusA gene because of the blocking neo-resistance gene (with its stop codons) and the gusA gene did not have its own promoter. Plants homozygous for construct 2 did not express gusA because it did not contain the gene. Plants were cross fertilized by removing the pollen from the inflorescence of a plant homozygous for construct 1 and pollinating with pollen from the inflorescence of a plant homozygous for construct 2.

Ninety six progeny plants were analyzed for GUS, and they all expressed GUS—both parents were negative for GUS activity, confirming the FLP catalyzed excision of the blocking neo-resistance gene resulting in positioning the CaMV 3.5 S promoter proximal to the gusA gene and thus allowing expression of gusA. Thus, gusA was silent until the T4 generation when it was activated by excision of the blocking DNA fragment by the FLP recombinase.

Example 4

Rice (*Oryza sativa*) plants were transformed using *Agrobacterium tumefaciens*-mediated treatment of callus obtained from mature seeds. Transformed, plants contained the following gene sequences:
1. CaMV35S promotor, LOX, hygromycin-resistance gene, LOX, promoterless gusA—
2. CaMV35S promotor, LOX, bar gene, LOX, promoterless gusA
3. CaMV35S, Cre, Ubiquitin promotor, bar gene
4. CaMV35S, Cre, Ubiquitin promotor, hygromycin-resistance gene T0 plants, hemizygous for one of the sequences 1-4, and which did not express GUS activity, were crossed in combinations such that the female contained constructs 1 or 2 and the male contained constructs 3 or 4, and vice versa. Progeny seeds were obtained and planted. The progeny were screened in the presence of the antibiotic hygromycin, or the herbicide Basta, and the progeny were analyzed for the presence of GUS activity. Since both parents were hemizygous for the constructs containing the lox sites or containing the Cre gene, the expected frequency of these constructs being present in progeny plants, if present and expressed as single genes, was 1 in 4 or 25%. That is, only 25% of the progeny have the potential for the recombinase to excise the blocking DNA (encoding the hygromycin resistance gene), which allows the CaMV35S promoter to drive expression of gusA. Table 2 shows that 19 of 75 (25.3%) plants analyzed expressed GUS. Southern blot analyses confirmed that in GUS expressing progeny plants, the blocking piece of DNA between the LOX sites had been removed.

TABLE 2

Rice Plants (Taipei 309) were crossed to test for Cre-induced excision of blocking DNA and resultant gus A transcription/translation, based on GUS activity in the progeny.

| Cross No. | Parent 1 (female) T0 Plant ID | Parent 2 (male) T0 Plant ID | T1 (Hybrid) Plant No. | No. of progeny T1 seed | Antibiotic[R] progeny Hyg(H) or ppt (P) | GUS+ progeny/ No. Tested |
|---|---|---|---|---|---|---|
| 1 | Cre/bar 108 | Lox/hph 90 | 6 | 8 | 4 (P) | 1/2 |
| 2 | Cre/bar 132 | Lox/hph 7 | 17 | 5 | 4 (P) | 1/4 |
| 3 | Cre/bar 226 | Lox/hph 511 | 131 | | | |
| | Cre/bar 226 | Lox/hph 511 | 134 | 20 | 5 (P) | 2/5 |
| | | TOTAL | | 33 | 13 (P) | 4/11 |

TABLE 2-continued

Rice Plants (Taipei 309) were crossed to test for Cre-induced excision of blocking DNA and resultant gus A transcription/translation, based on GUS activity in the progeny.

| Cross No. | Parent 1 (female) T0 Plant ID | Parent 2 (male) T0 Plant ID | T1 (Hybrid) Plant No. | No. of progeny T1 seed | Antibiotic[R] progeny Hyg(H) or ppt (P) | GUS+ progeny/ No. Tested |
|---|---|---|---|---|---|---|
| 1 | Cre/hph 405 | Lox/hph 27 | 51 | 24 | 17 (H) | 3/5 |
| 2 | Cre/hph 406 | Lox/hph 9 | 54 | 14 | 12 (H) | 3/11 |
| 3 | Cre/hph 406 | Lox/hph 3 | 93 | 24 | 15 (H) | 1/12 |
|   |             | TOTAL      |    | 62 | 44 (H) | 7/28 |
| 1 | Lox/hph 28  | Cre/hph 405 | 65 | 17 | 16 (H) | 4/16 |
|   |             | TOTAL      |    | 17 | 16 (H) | 4/16 |
| 1 | Lox/hph 29  | Cre/bar 132 | 27 | 10 | 9 (P)  | 2/8 |
| 2 | Lox/hph 512 | Cre/bar 227 | 128 | 19 | 10 (P) | 1/10 |
| 3 | Lox/hph 76  | Cre/bar 221 | 135 | 10 | 2 (P)  | 1/2 |
|   |             | TOTAL      |    | 39 | 21 (P) | 4/20 |
|   | Total of 10 crosses |    |    | 151 | 94 (H or P) | 19/75 |

Rice plants were also transformed with an *Agrobacterium tumefaciens*-mediated treatment of immature embryos with binary vector constructs containing the following gene sequences:

5. Ubiquitin promotor, FRT, neomycin phosphotransferase-resistance gene, FRTm, promoterless gusA, Ubiquitin promotor, hygromycin-resistance gene;
6. Ubiquitin promoter, FRT, neomycin phosphotransferase-resistance gene, FRTm, promoterless gusA, Ubiquitin promoter, bar gene;
7. Ubiquitin promotor, FLP, CaMV35S promoter, hygromycin-resistance gene;
8. Ubiquitin promoter, FLP, CaMV35S promoter, bar gene.

T0 plants, hemizygous for one of the sequences 5-8, and which did not express GUS activity were crossed in combinations such that the female contained constructs 5 or 6 and the male contained constructs 7 or 8, and vice versa. Progeny seeds were obtained and planted. The progeny were screened in the presence of the antibiotic hygromycin, or the herbicide Basta, and the progeny were analyzed for the presence of GUS activity. Since both parents were hemizygous for the constructs containing the FRT sites or containing the FLP gene, the expected frequency of these constructs being present in progeny plants, if present and expressed as single genes, was 1 in 4 or 25%. That is, only 25% of the progeny have the potential for the recombinase to excise the blocking DNA (encoding the neomycin phosphotransferase-resistance gene), which allows the ubiquitin promoter to drive expression of gusA. After a preliminary screening or selection on either hygromycin or PPT, 50% of the progeny should exhibit GUS activity, and Table 3 shows that 19 out of 31 plants analyzed expressed GUS. Southern analyses confirmed that in GUS expressing plants, the blocking piece of DNA between the FRT sites had been removed.

TABLE 3

Rice plants (Taipei 309) containing FRT sites were crossed with FLP-containing plants in order to test for FLP-mediated excision of blocking DNA and resultant GUS activity inprogeny plants.

| Cross No. | Parent 1 (female) T0 Plant ID | Parent 2 (male) T0 Plant ID | Antibiotic R or Herbicide R progeny-- Hyg (H) or PPT (P) | GUS+ progeny/ No. Tested |
|---|---|---|---|---|
| 1 | FLP/bar 24/6-15 | FRT/hph 201/6-15 | 2(H) | 1/2 |
|   | 61/7-3 | 23/6-19 | 1(H) | 1/1 |
| 2 | FRT/hph 201/16-19 | FLP/bar 61/7-3 | 14(P) | 8/14 |
|   | 201/16-19 | 60/7-3 | 1(P) | 0/1 |
|   | TOTAL |   | 15(P) | 8/15 |
| 3 | FRT/bar 12/8-28 | FLP/hph 4/6-19 | 2(H) | 2/2 |
|   | 27/8-28 | 2/6-19 | 2(H) | 2/2 |
|   | 80/8-28 | 200/6-19 | 1(H) | 1/1 |
|   | TOTAL |   | 5(H) | 5/5 |
| 4 | FRT/hph 201/6-19 | FLP hph 55/6-15 | 2(H) | 2/2 |
|   | TOTAL |   | 2(H) | 2/2 |
| 5 | FRT/bar 27/8-28 |   | 3(P) | 1/3 |
|   | 72/8-15 | FLP/bar | 6(P) | 3/6 |
|   | TOTAL |   | 9(P) | 4/9 |

Hyg = hygromycin, PPT-active ingredient of herbicide BASTA. The FLP- and FRT- containing plants were hemizygous, thus only 25% of the progeny would have the opportunity of having these two transgene constructs. GUS expression should occur in 50% of the progeny following selection on hygromycin or PPT. Statistical analysis was not done because the sample size is insufficient.

The invention claimed is:

1. A method for producing a compound, said method comprising the steps of
producing a fertile transgenic plant by introducing into plant cells a DNA construct comprising a promoter, a blocking sequence, and a coding sequence of a structural gene coding for a compound that is detrimental to the plant and is commercially valuable, said blocking sequence being flanked by a pair of directly repeated site-specific recombination sequences and wherein the coding sequence is operably linked to the promoter only after the removal of said blocking sequence, and culturing the plant cells to produce the fertile transgenic plant;
self-pollinating said transgenic plant to produce transgenic plants that are homozygous for the DNA construct;
crossing said transgenic plant homozygous for the DNA construct with a plant having a DNA sequence comprising a coding region encoding a site-specific recombinase that recognizes said site-specific recombination sequences to produce an F1 plant or seed;
expressing the site-specific recombinase in the F1 plant or seed;
expressing the compound; and
extracting the compound in economical quantities.

2. The method of claim 1 wherein the step of crossing said homozygous transgenic plant with a plant having a DNA sequence comprising a coding region encoding a site-specific recombinase produces and F1 plant or seed that expresses the biologically detrimental compound.

3. The method of claim 2, wherein the extracting step comprises extracting the compound from leaves of the plant or seed.

4. The method of claim 1 wherein the promoter is a constitutive promoter.

5. The method of claim 1 wherein the pair of directly repeated site-specific recombination sequences are FRT recombination sequences, and the coding region encoding the site-specific recombinase encodes the FLP recombinase and is operably linked to a constitutive promoter.

6. The method of claim 1 wherein the promoter of the DNA construct is a leaf-specific promoter and the extracting step includes extracting the compound from the leaves.

7. The method of claim 1 wherein the promoter of the DNA construct is a seed-specific promoter and the extracting step includes extracting the compound from the seeds.

* * * * *